(12) United States Patent
Suzuno

(10) Patent No.: US 11,580,858 B2
(45) Date of Patent: Feb. 14, 2023

(54) INFORMATION PROCESSING APPARATUS, INFORMATION PROCESSING METHOD, AND INFORMATION PROCESSING SYSTEM

(71) Applicant: SONY CORPORATION, Tokyo (JP)

(72) Inventor: Satoshi Suzuno, Saitama (JP)

(73) Assignee: SONY CORPORATION, Tokyo (JP)

( * ) Notice: Subject to any disclaimer, the term of this patent is extended or adjusted under 35 U.S.C. 154(b) by 163 days.

(21) Appl. No.: 16/996,247

(22) Filed: Aug. 18, 2020

(65) Prior Publication Data

US 2020/0394920 A1    Dec. 17, 2020

Related U.S. Application Data

(63) Continuation of application No. 15/964,941, filed on Apr. 27, 2018, now Pat. No. 10,783,788, which is a (Continued)

(30) Foreign Application Priority Data

Aug. 7, 2012 (JP) .................................. 2012-175274

(51) Int. Cl.
*G08G 1/16* (2006.01)
*G08G 1/00* (2006.01)
(Continued)

(52) U.S. Cl.
CPC .............. *G08G 1/166* (2013.01); *A61B 5/18* (2013.01); *G06V 20/597* (2022.01); *G08G 1/005* (2013.01);
(Continued)

(58) Field of Classification Search
CPC ...... G08G 1/166; G08G 1/005; G08G 1/0112; G08G 1/0129; G08G 1/0141;
(Continued)

(56) References Cited

U.S. PATENT DOCUMENTS

2007/0032929 A1   2/2007   Yoshioka et al.
2007/0167690 A1   7/2007   Miyazaki et al.
(Continued)

FOREIGN PATENT DOCUMENTS

JP     2003-123185 A     4/2003
JP     2004-348254 A     12/2004
(Continued)

OTHER PUBLICATIONS

Apr. 10, 2018, Japanese Office Action issued for related JP Application No. 2014-529386.

(Continued)

*Primary Examiner* — Rodney A Butler
(74) *Attorney, Agent, or Firm* — Paratus Law Group, PLLC

(57) ABSTRACT

An advice target location at which a user had a predetermined emotion, for example, is determined based on location information, user biological information, and user transportation means information, which have been acquired by a terminal device (20) being used by the user. Advice information containing information indicating an advice presentation region set by a server device (50) is generated based on the advice target location. This advice information is supplied from the server device (50) to the terminal device (20), so that the terminal device (20) presents advice. With this, advice as to locations pedestrians find dangerous can be presented to drivers, and advice as to locations drivers find dangerous can be presented to pedestrians. Accordingly, accidents and the like can be prevented.

9 Claims, 13 Drawing Sheets

Related U.S. Application Data continuation of application No. 14/414,914, filed as application No. PCT/JP2013/068139 on Jul. 2, 2013, now Pat. No. 9,978,279.

(51) Int. Cl.
| | |
|---|---|
| *G08G 1/01* | (2006.01) |
| *G08G 1/09* | (2006.01) |
| *G08G 1/005* | (2006.01) |
| *G08G 1/0962* | (2006.01) |
| *G08G 1/0967* | (2006.01) |
| *A61B 5/18* | (2006.01) |
| *G06V 20/59* | (2022.01) |
| *A61B 5/024* | (2006.01) |

(52) U.S. Cl.
CPC ......... *G08G 1/0112* (2013.01); *G08G 1/0129* (2013.01); *G08G 1/0141* (2013.01); *G08G 1/0962* (2013.01); *G08G 1/096716* (2013.01); *G08G 1/096741* (2013.01); *G08G 1/096775* (2013.01); *A61B 5/02438* (2013.01)

(58) Field of Classification Search
CPC ........... G08G 1/0962; G08G 1/096716; G08G 1/096741; G08G 1/096775; A61B 5/02438; A61B 5/18; G06V 20/597
USPC .......................................................... 701/45
See application file for complete search history.

(56) References Cited

U.S. PATENT DOCUMENTS

| | | |
|---|---|---|
| 2011/0106736 A1 | 5/2011 | Aharonson et al. |
| 2015/0304817 A1 | 10/2015 | Yorifuji |
| 2018/0259959 A1* | 9/2018 | Yamada ............... G05D 1/0282 |
| 2020/0143940 A1* | 5/2020 | Yasui ..................... G06Q 50/22 |

FOREIGN PATENT DOCUMENTS

| | | |
|---|---|---|
| JP | 3848554 B2 | 9/2006 |
| JP | 2008-062852 A | 3/2008 |
| JP | 2009-146254 A | 7/2009 |
| JP | 2010-244554 A | 10/2010 |
| JP | 2011-209919 A | 10/2011 |
| JP | 2012-048310 A | 3/2012 |

OTHER PUBLICATIONS

Aug. 19, 2016, Chinese Communication issued for related CN Application No. 201380040366.5.
Feb. 23, 2016, Chinese Office Action issued for related CN Application No. 201380040366.5.
Mar. 30, 2016, Extended European Search Report issued for EP Application No. 13827815.5.
Oct. 24, 2017, Japanese Office Action issued for related JP Application No. 2014-529386.
Apr. 4, 2017, Japanese Communication issued for related JP Application No. 2014-529386.

* cited by examiner

FIG. 8A

| TIME | HEART BEATS IN 10 SECONDS |
|---|---|
| 2012/05/18 9:30:40-49 | 6 |
| 2012/05/18 9:30:50-59 | 7 |
| 2012/05/18 9:31:00-09 | 12 |
| 2012/05/18 9:30:10-19 | 9 |
| 2012/05/18 9:30:10-19 | 8 |
| . . . | |

FIG. 8B

| TIME | LATITUDE/LONGITUDE | TRANSPORTATION MEANS |
|---|---|---|
| 2012/05/18 9:30:40-49 | xx.6894875, yyy.6917064 | VEHICLE |
| 2012/05/18 9:30:50-59 | xx.6894886, yyy.6917155 | VEHICLE |
| 2012/05/18 9:31:00-09 | xx.6894934, yyy.6917221 | VEHICLE |
| 2012/05/18 9:30:10-19 | xx.6894956, yyy.6917333 | VEHICLE |
| 2012/05/18 9:30:10-19 | xx.6894977, yyy.6917711 | VEHICLE |
| . . . | | |

FIG. 8C

| TIME | LATITUDE/LONGITUDE | TRANSPORTATION MEANS |
|---|---|---|
| 2012/05/18 9:31:00-09 | xx.6894934, yyy.6917221 | VEHICLE |
| . . . | | |

*FIG. 10*

| TIME | LATITUDE/LONGITUDE | TRANSPORTATION MEANS |
|---|---|---|
| 2012/05/18 9:31:00-09 | xx. 6894934, yyy. 6917221 | VEHICLE |
| 2012/05/18 9:31:30-39 | vv. 6895964, www. 6934951 | VEHICLE |
| 2012/05/19 7:23:20-29 | uu. 5891234, zzz. 6917432 | VEHICLE |

| TIME | LATITUDE/LONGITUDE | TRANSPORTATION MEANS |
|---|---|---|
| 2012/05/13 07:22:30-39 | vv. 6333334, yyy. 6910024 | VEHICLE |
| 2012/05/23 12:11:10-19 | xx. 6894235, yyy. 6917021 | VEHICLE |
| 2012/05/23 13:31:20-29 | vv. 8456923, zzz. 3537952 | VEHICLE |

| TIME | LATITUDE/LONGITUDE | TRANSPORTATION MEANS |
|---|---|---|
| 2012/05/13 13:31:10-19 | xx. xx94021, yyy. 6917220 | VEHICLE |
| 2012/05/17 12:31:00-09 | uu. 5226662, yyy. 3435178 | VEHICLE |
| 2012/05/18 22:31:50-59 | xx. 9973433, yyy. 4345423 | VEHICLE |

| TIME | LATITUDE/LONGITUDE | TRANSPORTATION MEANS |
|---|---|---|
| 2012/05/13 15:31:20-29 | xx. 5842424, yyy. 4242525 | VEHICLE |
| 2012/05/22 19:31:10-19 | vv. 3254256, zzz. 4252525 | VEHICLE |
| 2012/05/28 12:31:00-09 | xx. xx94921, yyy. 6917210 | VEHICLE |

| TIME | LATITUDE/LONGITUDE | TRANSPORTATION MEANS |
|---|---|---|
| 2012/05/10 12:31:40-49 | xx. 4141143, zzz. 6242424 | VEHICLE |
| 2012/05/11 15:31:30-39 | xx. 6894544, yyy. 6917325 | VEHICLE |
| 2012/05/12 21:31:00-09 | xx. 6894600, yyy. 6917426 | VEHICLE |

INFORMATION PROCESSING APPARATUS, INFORMATION PROCESSING METHOD, AND INFORMATION PROCESSING SYSTEM

CROSS-REFERENCE TO PRIOR APPLICATION

This application is a continuation of U.S. patent application Ser. No. 15/964,941 (filed on Apr. 27, 2018), which is a continuation of U.S. patent application Ser. No. 14/414,914 (filed on Jan. 15, 2015 and issued as U.S. Pat. No. 9,978,279 on May 22, 2018), which is a National Stage Patent Application of PCT International Patent Application No. PCT/JP2013/068139 (filed on Jul. 2, 2013) under 35 U.S.C. § 371, which claims priority to Japanese Patent Application No. 2012-175274 (filed on Aug. 7, 2012), which are all hereby incorporated by reference in their entirety.

TECHNICAL FIELD

This technique relates to information processing apparatuses, information processing methods, and an information processing system, and enables presentation of effective advice for drivers, pedestrians, and the like to prevent accidents and the like.

BACKGROUND ART

There have been apparatuses suggested for assisting driving of a vehicle by collecting information about driving of vehicles, determining situations, providing information to the driver, and controlling operation of the vehicle. For example, according to Patent Document 1, an emotion of a driver is estimated by combining changes in the biological conditions (such as the heart rate, blood pressure, and respiration) of the driver with changes in the vehicle conditions (such as the condition of driving by the driver, the existence/nonexistence of an object in the surrounding area, and contact with an object in the surrounding area). In this manner, the state of mind of the driver is determined holistically. Further, there has been a suggestion for performing appropriate automatic control by feeding a result of emotion estimation back to determination on the conditions of the vehicle and recognizing the conditions of the vehicle in greater detail.

CITATION LIST

Patent Document

Patent Document 1: Japanese Patent Application Laid-Open No. 2008-62852

SUMMARY OF THE INVENTION

Problems to be Solved by the Invention

A traffic accident between a vehicle and a pedestrian (a bicycle) is caused by carelessness on one or both sides. Therefore, in many cases, traffic accidents can be prevented if both sides pay enough attention. However, there are differences between the locations drivers find dangerous and the locations pedestrians find dangerous in terms of traffic. Therefore, there are cases where a location determined to be dangerous by drivers is not regarded as a dangerous location by pedestrians, or where a location determined to be dangerous by pedestrians is not regarded as a dangerous location by drivers. In such cases, even if one side is careful, the other side is not paying enough attention, and there is a risk of an accident.

In view of the above, this technique aims to provide information processing apparatuses, information processing methods, and an information processing system that can present effective advice for preventing accidents and the like to drivers, pedestrians, and the like.

Solutions to Problems

A first aspect of this technique lies in an information processing apparatus that includes: a determining unit that determines an advice target location at which advice needs to be presented for each transportation means based on location information, biological information, and transportation means information; and a presentation region setting unit that sets an advice presentation region where advice is to be presented based on the advice target location determined by the determining unit.

In this technique, an advice target location at which advice needs to be presented for each transportation means is determined based on information in which location information, biological information, and transportation means information are associated with one another. For example, an emotion is estimated based on the biological information contained in the reception information in which the location information, the biological information, and the transportation means information are associated with one another, and the location of acquirement of the biological information in a case where a predetermined emotion is estimated is determined to be the advice target location. In determining the advice target location, geographical conditions are also taken into account. Further, the location information is corrected so as to indicate a location on a street. The advice presentation region is set based on the determined advice target location. For example, advice presentation candidate regions are set by dividing a region of a street, statistical processing is performed on a result of determination on an advice target location in an advice presentation candidate region, the advice presentation candidate region is set as an advice presentation region based on a result of the processing. In a case where a request for advice information has been issued, an advice presentation region is selected based on the location indicated by the location information indicated by the request for the advice information, and the advice information indicating the selected advice presentation region is generated and is transmitted to the requester that has requested the advice information. The advice information is also transmitted in such a manner that the transportation means on which the advice presentation region is based is distinguishable. The advice information also includes presentation information indicating what kind of advice is to be presented.

A second aspect of this technique lies in an information processing method that includes: the step of determining an advice target location at which advice needs to be presented for each transportation means based on location information, biological information, and transportation means information; and the step of setting an advice presentation region based on the determined advice target location.

A third aspect of this technique lies in an information processing apparatus that includes: a location information acquiring unit that acquires location information; a biological information acquiring unit that acquires biological information about a user; a transportation means identifying unit that identifies the transportation means of the user; a communication unit; a control unit that transmits the location information acquired by the location information acquiring unit, the biological information acquired by the biological information acquiring unit, and transportation means information indicating the transportation means identified by the transportation means identifying unit from the communication unit to an information processing apparatus that provides advice information, the location information, the biological information, and the transportation means information being associated with one another; and an advice presenting unit that presents advice based on the advice information received by the communication unit.

In this technique, the location information acquired by the location information acquiring unit, the biological information acquired by the biological information acquiring unit, and the transportation means information indicating the transportation means identified by the transportation means identifying unit are associated with one another, and are transmitted to an information processing apparatus that provides advice information. In a case where advice information about a predetermined range based on a desired location has not been acquired, the control unit transmits a request for the advice information to the information processing apparatus that provides the advice information. The request for the advice information contains location information indicating the desired location. The advice presenting unit determines an advice presentation region through which the information processing apparatus is about to pass based on information about the advice presentation region, the information being contained in the received advice information, and presents advice as to the determined advice presentation region. In a case where the advice information contains presentation information indicating what kind of advice is to be presented, advice is presented based on the presentation information. In a case where an emotion estimating unit is further provided, an emotion of the user is estimated based on acquired biological information, and location information indicating the location of acquirement of the biological information in a case where a predetermined emotion is estimated is associated with the transportation means information, and is transmitted to the information processing apparatus that provides the advice information.

A fourth aspect of this technique lies in an information processing method that includes: the step of acquiring location information; the step of acquiring biological information about a user; the step of identifying the transportation means of the user; the step of transmitting the acquired location information, the acquired biological information, and transportation means information indicating the identified transportation means to an information processing apparatus that provides advice information, the acquired location information, the acquired biological information, and the transportation means information being associated with one another; and the step of receiving the advice information and presenting advice.

A fifth aspect of this technique lies in an information processing system formed with a first information processing apparatus and a second information processing apparatus. In this information processing system, the first information processing apparatus includes: a location information acquiring unit that acquires location information; a biological information acquiring unit that acquires biological information about a user; a transportation means identifying unit that identifies the transportation means of the user; a communication unit that communicates with the second information processing apparatus; a control unit that transmits the location information acquired by the location information acquiring unit, the biological information acquired by the biological information acquiring unit, and transportation means information indicating the transportation means identified by the transportation means identifying unit from the communication unit to the second information processing apparatus that provides advice information, the location information, the biological information, and the transportation means information being associated with one another; and an advice presenting unit that presents advice based on the advice information received by the communication unit. The second information processing apparatus includes: a communication unit that communicates with the first information processing apparatuses; a determining unit that determines an advice target location at which advice needs to be presented for each transportation means based on reception information containing location information, biological information, and transportation means information associated with one another, the reception information being received by the communication unit; a presentation region setting unit that sets an advice presentation region based on the advice target location determined by the determining unit; and an advice information transmission processing unit that transmits advice information indicating the advice presentation region to the requester that has requested the advice information.

Effects of the Invention

According to this technique, an advice target location at which a user had a predetermined emotion, for example, is determined for each transportation means based on location information, biological information, and transportation means information, and an advice presentation region is set based on the advice target location. Also, advice as to the set advice presentation region is presented. Accordingly, effective advice for preventing accidents can be presented to users such as drivers or pedestrians. For example, locations pedestrians find dangerous can be presented to drivers, and locations drivers find dangerous can be presented to pedestrians. Accordingly, accidents and the like can be prevented. It should be noted that the effects described in this specification are merely examples and do not limit the present technique, and there may be additional effects.

BRIEF DESCRIPTION OF DRAWINGS

FIGS. 8A-8C show an example operation in the advice target location determining process.

FIG. 10 is a diagram for explaining an operation in the advice presentation region setting process.

MODES FOR CARRYING OUT THE INVENTION

The following is a description of embodiments for carrying out the present technique. Explanation will be made in the following order.

1. System configuration
2. Structure of a terminal device
3. Structure of a server device
4. Operations of a terminal device and the server device
5. Other structures and operations <1. System Configuration>

Figure 1:
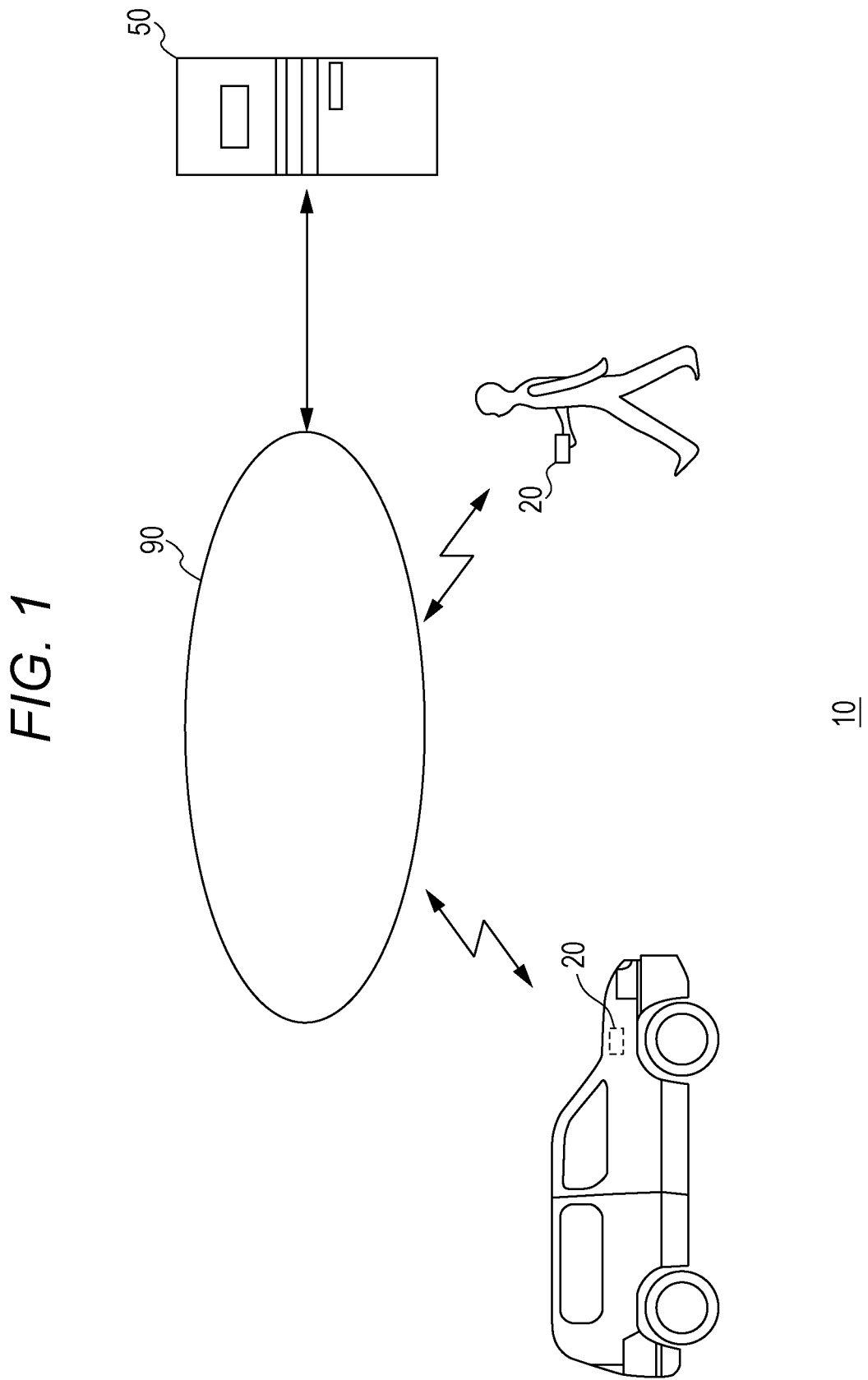
FIG. 1 is a diagram showing an example configuration of an information processing system.

FIG. 1 shows an example configuration of an information processing system. The information processing system 10 is formed with first information processing apparatuses (hereinafter referred to as "terminal devices") 20 to be used by a driver, a pedestrian, and the like, and a second information processing apparatus (hereinafter referred to as the "server device") 50 to supply advice information to the first information processing apparatuses 20.

The terminal devices 20 are connected to the server device 50 via a network 90 such as a public communication network. A terminal device 20 generates location information and biological information about the user who is using the terminal device 20. The terminal device 20 or the server device 50 determines an advice target location based on the location information, the biological information, and the like, which have been generated by the terminal device 20. The server device 50 performs statistical processing on the result of the determination made on the advice target location based on the location information, the biological information, and the like, which have been generated by each terminal device 20, and sets an advice presentation region. In a case where a terminal device 20 presents advice to a user, the advice is presented based on advice information supplied from the server device 50. The server device 50 selects an advice presentation region based on the current location of the terminal device 20, for example, and supplies advice information containing information indicating the selected advice presentation region to the terminal device 20, so that advice can be presented.

In the description below, the server device 50 determines an advice target location, advice information is supplied from the server device 50 to a terminal device 20, so that advice is presented. A notification of a place determined to be dangerous for drivers and pedestrians is issued as advice in the description below.

<2. Structure of a Terminal Device>

A terminal device 20 has a function to display a current location on a map, a navigation function to indicate a path to a destination, and the like. The terminal device 20 communicates with the server device 50, and presents advice to a user on a displayed map or with voice based on advice information supplied from the server device 50.

Figure 2:
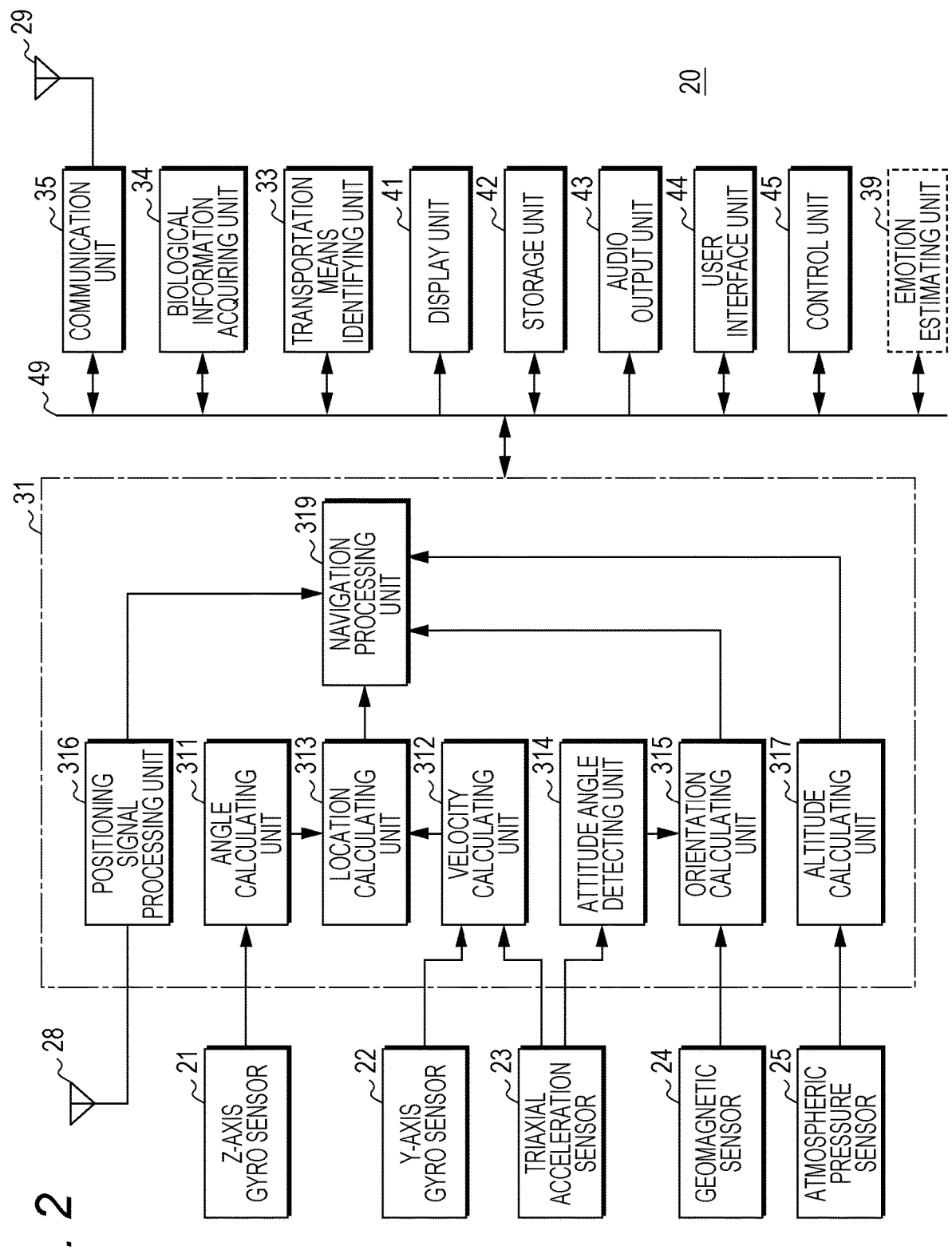
FIG. 2 is a diagram showing an example structure of a terminal device.

FIG. 2 shows an example structure of the terminal device 20. The terminal device 20 includes a Z-axis gyro sensor 21, a Y-axis gyro sensor 22, a triaxial acceleration sensor 23, a geomagnetic sensor 24, an atmospheric pressure sensor 25, and antennas 28 and 29. The terminal device 20 also includes a navigation unit 31, a transportation means identifying unit 33, a biological information acquiring unit 34, a communication unit 35, a display unit 41, a storage unit 42, an audio output unit 43, a user interface unit 44, and a control unit 45. The navigation unit 31 as a location information acquiring unit includes an angle calculating unit 311, a velocity calculating unit 312, a location calculating unit 313, an attitude angle detecting unit 314, an orientation calculating unit 315, a positioning signal processing unit 316, an altitude calculating unit 317, and a navigation processing unit 319. Further, an emotion estimating unit 39 may be provided as described later.

Figure 3:
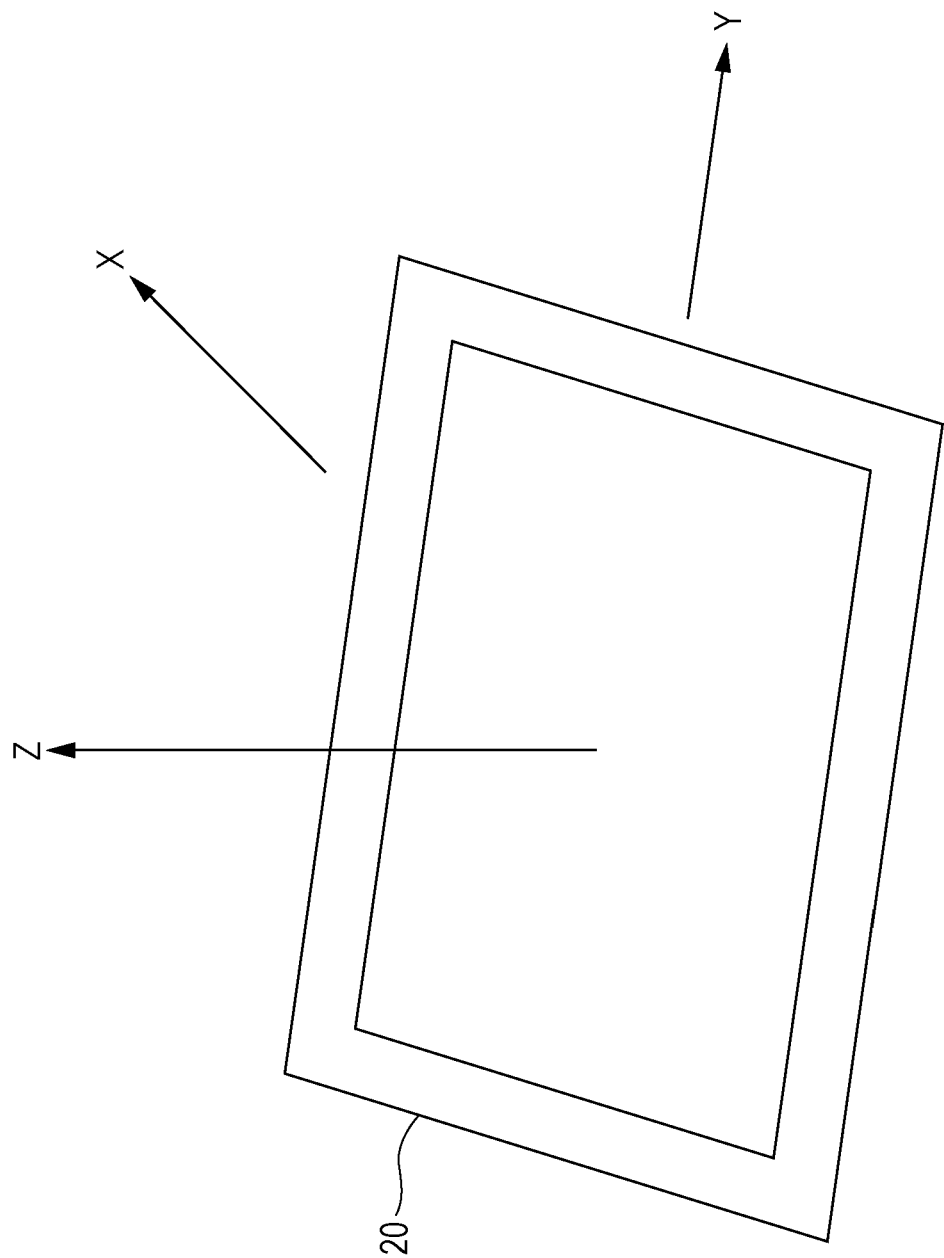
FIG. 3 is a diagram showing the relationship between the axis of a Z-axis gyro sensor and directions.

The Z-axis gyro sensor 21 detects yawing, which is movement about the Z-axis. The Z-axis gyro sensor 21 detects a yaw rate wz that is the velocity (angular velocity) at which the angle of rotation of the terminal device 20 about the Z-axis changes. The Z-axis gyro sensor 21 detects a yaw rate at a sampling frequency of 50 Hz, for example, and outputs a detection signal indicating the detected yaw rate to the angle calculating unit 311 of the navigation unit 31. As shown in FIG. 3, the Z-axis corresponds to the vertical direction. The X-axis corresponds to the traveling direction of the terminal device 20, and the Y-axis corresponds to the horizontal direction perpendicular to the X-axis.

The angle calculating unit 311 calculates the angle at which the terminal device 20 rotates by integrating the yaw rate wz input from the Z-axis gyro sensor 21 and the sampling frequency, and outputs angle data indicating the calculated angle to the location calculating unit 313.

The Y-axis gyro sensor 22 detects pitching, which is movement about the Y-axis. The Y-axis gyro sensor 22 detects a pitch rate wy as the angular velocity about the Y-axis at a sampling frequency of 50 Hz, for example, and outputs a detection signal indicating the detected pitch rate to the velocity calculating unit 312.

The triaxial acceleration sensor 23 detects an acceleration Ax about the X-axis, an acceleration Ay about the Y-axis, and an acceleration Az about the Z-axis. The triaxial acceleration sensor 23 detects the acceleration Ax, the acceleration Ay, and the acceleration Az at a sampling frequency of 50 Hz, for example, and inputs a detection signal indicating the detected frequencies to the velocity calculating unit 312 and the attitude angle detecting unit 314.

The velocity calculating unit 312 calculates a velocity V in the traveling direction by dividing the Z-axis acceleration Az supplied from the triaxial acceleration sensor 23 by the pitch rate wy supplied from the Y-axis gyro sensor 22. The velocity calculating unit 312 outputs velocity data indicating the calculated velocity to the location calculating unit 313.

The location calculating unit 313 calculates location information about the current location based on the velocity calculated by the velocity calculating unit 312 and the angle calculated by the angle calculating unit 311. Specifically, the location calculating unit 313 calculates a change from the previously calculated location to the current location based on the velocity and the angle. The location calculating unit 313 then calculates current location information from the change and the previous location. After that, the location calculating unit 313 supplies the location information about the current location to the navigation processing unit 319.

The attitude angle detecting unit 314 performs a predetermined attitude angle detecting process based on the detection signal supplied from the triaxial acceleration sensor 23, to generate and output attitude angle data indicating the attitude angle of the terminal device to the orientation calculating unit 315.

The geomagnetic sensor 24 detects geomagnetism in each of the X-, Y-, and Z-axis directions, and outputs geomagnetic data indicating the detection result to the orientation calculating unit 315.

The orientation calculating unit 315 performs a predetermined correcting process on the geomagnetic data supplied from the geomagnetic sensor 24, and generates orientation data indicating the orientation of the terminal device 20 based on the corrected geomagnetic data and the attitude angle data supplied from the attitude angle detecting unit 314. The orientation calculating unit 315 outputs the generated orientation data to the navigation processing unit 319.

That is, the triaxial acceleration sensor 23, the geomagnetic sensor 24, the attitude angle detecting unit 314, and the orientation calculating unit 315 function as an electromagnetic compass, and generate orientation data. Mostly, when the terminal device 20 is detached from the vehicle and is used (when the terminal device 20 is used while the user is walking, for example), the navigation processing unit 319 can provide the user with map data indicating the orientation of the terminal device 20 based on the orientation data. When used on a vehicle, the terminal device 20 associates a street in the map data with the location of the vehicle in accordance with the pathway of the location of the vehicle, and can provide the user with map data in which the orientation of the terminal device 20 is adjusted based on the orientation of the map.

The antenna 28 receives positioning signals from positioning satellites, such as signals from GPS (Global Positioning System) satellites, and outputs the received signals to the positioning signal processing unit 316. The received positioning signals contain information such as orbit data indicating the orbits of the positioning satellites, and signal transmission times.

The positioning signal processing unit 316 calculates the locations of the respective positioning satellites from orbit data obtained by demodulating the received signals supplied from the antenna 28, and calculates the distances from the respective positioning satellites to the terminal device 20 from differences between the transmission times and the reception times of the positioning signals. The current three-dimensional location is then calculated based on the calculated locations of the respective positioning satellites, and the distances from the respective positioning satellites to the terminal device 20. The positioning signal processing unit 316 generates and outputs current location data indicating the calculated three-dimensional location to the navigation processing unit 319.

The atmospheric pressure sensor 25 is a sensor that detects ambient pressure. The atmospheric pressure sensor 25 detects atmospheric pressure at a sampling frequency of 50 Hz, for example, and outputs the detected atmospheric pressure data to the altitude calculating unit 317.

The altitude calculating unit 317 calculates the altitude of the terminal device 20 based on the atmospheric pressure data supplied from the atmospheric pressure sensor 25, and supplies altitude data indicating the calculated altitude to the navigation processing unit 319.

The navigation processing unit 319 can acquire the current location information from the location calculating unit 313 or the positioning signal processing unit 316, and can further acquire the orientation of the terminal device 20 from the orientation calculating unit 315 and the altitude of the terminal device 20 from the altitude calculating unit 317. That is, the navigation processing unit 319 has not only an absolute location acquirement function but also a relative location acquirement function using various kinds of sensors. However, relative location information may be used in a situation where the terminal device 20 exists at such a location that an absolute location cannot be acquired or positioning signals cannot be received, or may be used in conjunction with absolute location information.

The navigation processing unit 319 also reads peripheral map data containing the current location from the storage unit 42, and generates a map image based on the orientation data. The map image contains the current location and conforms to the current orientation of the terminal device 20. The navigation processing unit 319 displays the generated map image on the screen of the display unit 41. The navigation processing unit 319 can use information about the acquired location as it is, but may perform various kinds of correction on the information. A typical example of a correcting process is a map matching process. A map matching process is a technique of correcting location information errors by using map information. Through the map matching process, the corresponding street on the map is searched for in accordance with a change in the location information, correct location information is estimated, and the location information is corrected based on this estimation.

The transportation means identifying unit 33 identifies the transportation means in which the terminal device 20 is used, and generates transportation means identification information. In a case where an acceleration sensor, gyro sensor, or the like is used in the terminal device 20, for example, the transportation means identifying unit 33 carries out an action analysis based on sensor signals generated by these sensors, and identifies the transportation means based on a result of the analysis. In a case where the terminal device 20 is secured to a vehicle via a cradle, for example, the transportation means identifying unit 33 determines the transportation means to be a vehicle as the attachment to the cradle is detected. The transportation means identifying unit 33 may determine a transportation means by using the velocity calculated by the velocity calculating unit 312, the angle calculated by the angle calculating unit 311, and the like. In a case where attachment to a cradle has not been detected, if the velocity exceeds a predetermined velocity, for example, the transportation means is determined to be a bicycle or the like. If the velocity is lower than the predetermined velocity, the transportation means is determined to be walking. In this manner, the transportation means identifying unit 33 identifies the transportation means in which the terminal device 20 is used, and generates the transportation means information. The transportation means identifying unit 33 may allow the user to input which transportation means the user is using.

The biological information acquiring unit 34 acquires biological information about the driver, the pedestrian, or the like, who is using the terminal device 20. The biological information acquiring unit 34 is formed with a heart rate sensor, a blood pressure sensor, a respiration sensor, a perspiration sensor, a brain wave sensor, a myoelectric sensor, and the like, so that the emotion being felt by the driver, the pedestrian, or the like can be analyzed based on detection signals from the respective sensors.

The antenna 29 is connected to the communication unit 35. The communication unit 35 communicates with a base station (not shown) via the antenna 29, and connects to the server device 50 via the public communication network 90. The communication unit 35 outputs the location information (the current location and the current altitude) acquired by the navigation unit 31, the transportation means information generated by the transportation means identifying unit 33, and the biological information acquired by the biological information acquiring unit 34, to the server device 50. The communication unit 35 also receives advice information supplied from the server device 50.

The display unit 41 is a display device that outputs a screen that has information indicating the current location superimposed on map data, for example. The display unit 41 also displays a menu for selecting a function of the terminal device 20 and performing various settings and the like. The display unit 41 further presents advice on the screen based on advice information supplied from the server device 50. The display unit 41 is formed with a display device such as a liquid crystal display (LCD), an organic EL (electroluminescence) display, or the like.

The storage unit 42 is a storage medium that stores the program for the terminal device 20 to operate, map data, and biological information and transportation means identification information associated with time information as a log. This storage unit 42 may be a nonvolatile memory such as a flash ROM (or a flash memory), an EEPROM (Electrically Erasable Programmable Read-Only Memory), or an EPROM (Erasable Programmable ROM), a magnetic disk such as a hard disk or a disk-shaped magnetic body, an optical disk such as a CD (Compact Disc), a DVD-R (Digital Versatile Disc Recordable), or a BD (Blu-Ray Disc (a registered trade name)), or a storage medium such as an MO (Magneto Optical) disk.

The audio output unit 43 is an output device that outputs audio data, and is formed with a speaker or the like. The audio output unit 43 outputs audio guidance related to navigation, for example. The user can recognize the path to take by listening to the audio guidance, without looking at the display unit 41. The audio output unit 43 also presents audio advice based on advice information supplied from the server device 50.

The user interface unit 44 is formed with operation switches, operation buttons, a touch panel integrated with the screen of the display unit 41, or the like. The user interface unit 44 receives an operation instruction from the user, and outputs an operation signal indicating the contents of the operation to the control unit 45. The operation instruction from the user may be a destination setting, an enlargement or reduction of the map, an audio guidance setting, or a screen display setting, for example. This user interface unit 44 may be a touch screen integrally formed with the display unit 41. Alternatively, the user interface unit 44 may be a physical structure provided separately from the display unit 41, such as buttons, switches, or levers. The user interface unit 44 may be a signal receiving unit that detects an operation signal indicating an operation instruction from the user via a remote controller.

The control unit 45 controls operations of the respective components based on an operation signal from the user interface unit 44, and causes the terminal device 20 to operate in accordance with a user operation. The control unit 45 is formed with a CPU (Central Processing Unit), a ROM (Read Only Memory), a RAM (Random Access Memory), and the like. The CPU executes a program stored in the ROM or the storage unit 42, to control operations of the respective components based on an operation signal from the user interface unit 44, and cause the terminal device 20 in accordance with a user operation. The control unit 45 associates the location information, the biological information, and the transportation means information with one another, and transmits these pieces of information from the communication unit 35 to the server device 50 that provides advice information. The control unit 45 further causes the display unit 41 or the audio output unit 43 to present advice based on the current location and received advice information.

<3. Structure of the Server Device>

The server device 50 performs a process of determining an advice target location based on information supplied from a terminal device 20, a process of setting an advice presentation region through statistical processing performed on the advice target location determined for each terminal device, a provision of advice information to a terminal device 20, and the like.

Figure 4:
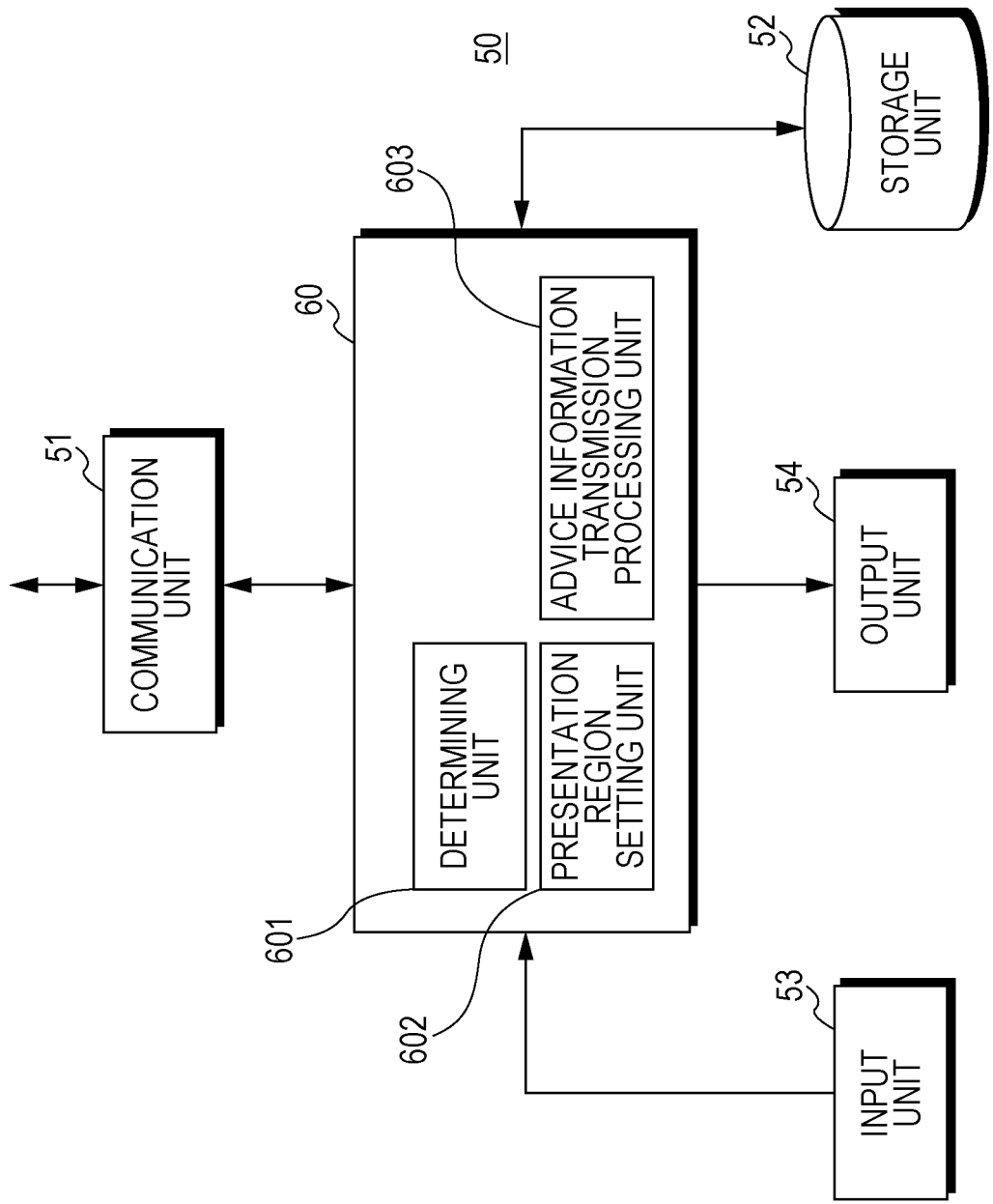
FIG. 4 is a diagram showing an example structure of a server device.

FIG. 4 shows an example structure of the server device. The server device 50 includes a communication unit 51, a storage unit 52, an input unit 53, an output unit 54, and a control unit 60, and the communication unit 51, the storage unit 52, the input unit 53, and the output unit 54 are connected to the control unit 60.

The communication unit 51 communicates with a terminal device 20 via a public communication line or the like. The communication unit 51 supplies information supplied from the terminal device 20 to the control unit 60. The communication unit 51 also transmits information supplied from the control unit 60 to the terminal device 20.

The storage unit 52 stores the information supplied from the terminal device 20 and information generated by the control unit 60. The storage unit 52 is formed with a HDD (Hard Disk Drive), a nonvolatile memory, or the like.

The input unit 53 is formed with a keyboard, a pointing device, and the like, and inputs information and the like. The output unit 54 is formed with a liquid crystal display and the like, and displays information or the like stored in the storage unit 52.

The control unit 60 is formed with a CPU (Central Processing Unit), a ROM (Read Only Memory), a RAM (Random Access Memory), and the like. The CPU performs various kinds of processes in accordance with a program recorded on the ROM or the storage unit 52. Necessary data for the CPU to perform various kinds of processes is also stored in the RAM as appropriate.

The control unit 60 also includes a determining unit 601, a presentation region setting unit 602, and an advice information transmission processing unit 603.

The determining unit 601 determines an advice target location at which advice needs to be presented for each transportation means based on information supplied from each terminal device 20. For example, the determining unit 601 estimates an emotion based on biological information supplied from each terminal device 20, and determines the advice target location to be the location indicated by the location information associated with the biological information in a case where a predetermined emotion is estimated. For example, a location at which an emotion of surprise is estimated through detection of an increase in the heart rate, an increase in blood pressure, perspiration, or the like is determined to be the advice target location.

The presentation region setting unit 602 sets an advice presentation region based on the determined advice target location. For example, the presentation region setting unit 602 performs statistical processing on the determined advice target location for each transportation means, and sets an advice presentation region that is the region where a predetermined emotion is estimated the largest number of times.

The advice information transmission processing unit 603 performs a process of transmitting advice information indicating the advice presentation region to the advice information requester. Also, as information about the transportation means is included in the advice information, it is possible to recognize that the advice is based not only on its own transportation means but also on a different transportation means from its own transportation means.

<4. Operations of a Terminal Device and the Server Device>

Figure 5:
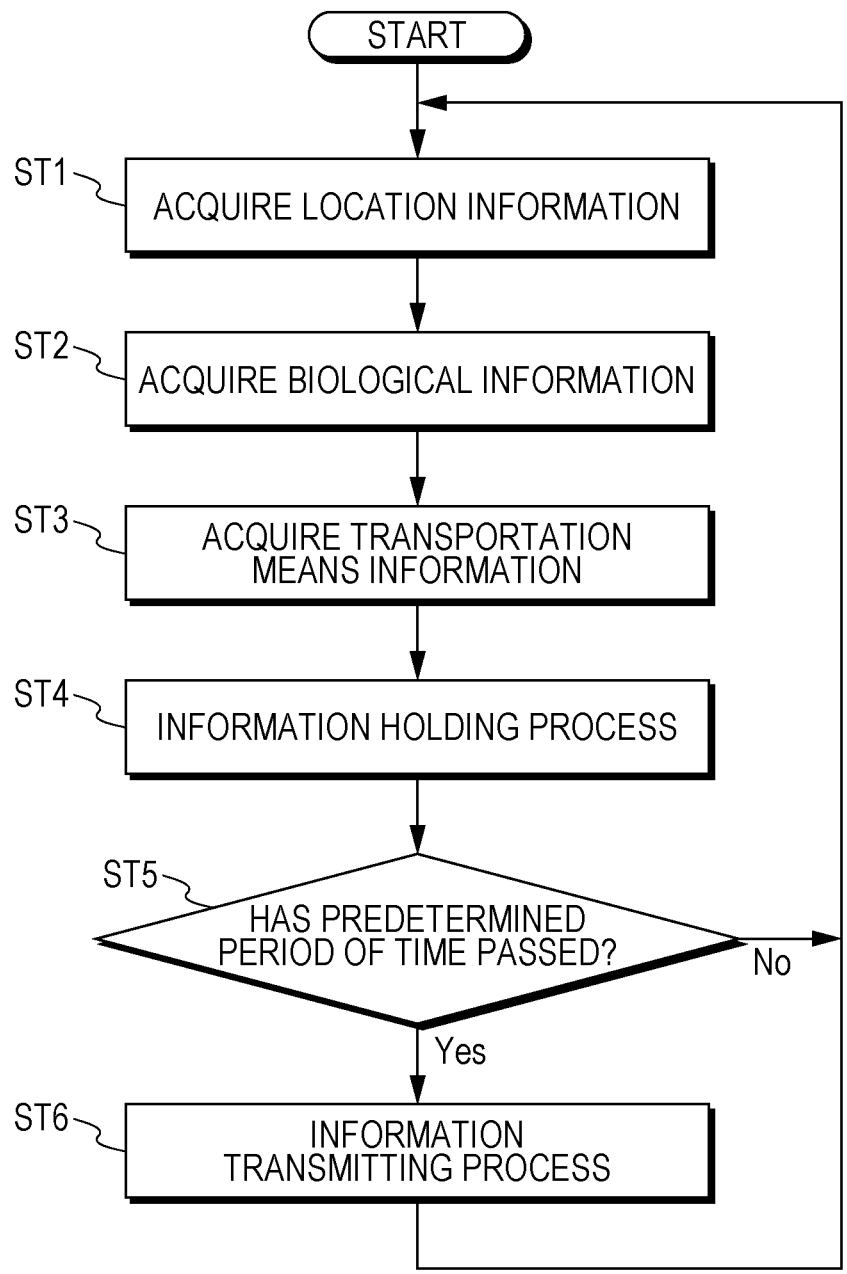
FIG. 5 is a flowchart showing an information providing operation of a terminal device.

Next, operations of a terminal device and the server device are described. FIG. 5 is a flowchart showing an information providing operation of a terminal device 20. In step ST1, the terminal device 20 acquires location information. The terminal device 20 acquires location information through the navigation unit 31, and then moves on to step ST2. The location information may contain not only information indicating latitude and longitude, but also information indicating altitude.

In step ST2, the terminal device 20 acquires biological information. The terminal device 20 acquires biological information about the driver, the pedestrian, or the like, who is using the terminal device 20, through the biological information acquiring unit 34, and then moves on to step ST3.

In step ST3, the terminal device 20 acquires transportation means information. The terminal device 20 generates the transportation means information indicating the transportation means identified by the transportation means identifying unit 33, and then moves on to step ST4.

In step ST4, the terminal device 20 performs an information holding process. The terminal device 20 associates the acquired location information, biological information, and transportation means information with one another, holds these pieces of information as a log, and then moves on to step ST5. The association among the location information, the biological information, and the transportation means information is made with the use of time information, for example, and the location information, the biological information, and the transportation means information are associated with information about the same time.

In step ST5, the terminal device 20 determines whether a predetermined period of time has passed. The terminal device 20 returns to step ST1 if the predetermined period of time has not passed yet, and moves on to step ST6 if the predetermined period of time has passed.

In step ST6, the terminal device 20 performs an information transmitting process. The terminal device 20 transmits the unsent log being held therein, or the location information, the transportation means information, and the biological information associated with one another, together with the time information, from the communication unit 35 to the server device 50, and then returns to step ST1.

The procedures of steps ST1 through ST3 may be carried out in different order from the order shown in FIG. 5, or may be carried out in parallel. Although information is transmitted to the server device 50 every time a predetermined period of time has passed in the process shown in FIG. 5, information may be transmitted every time the amount of information being held reaches a predetermined amount.

Figure 6:
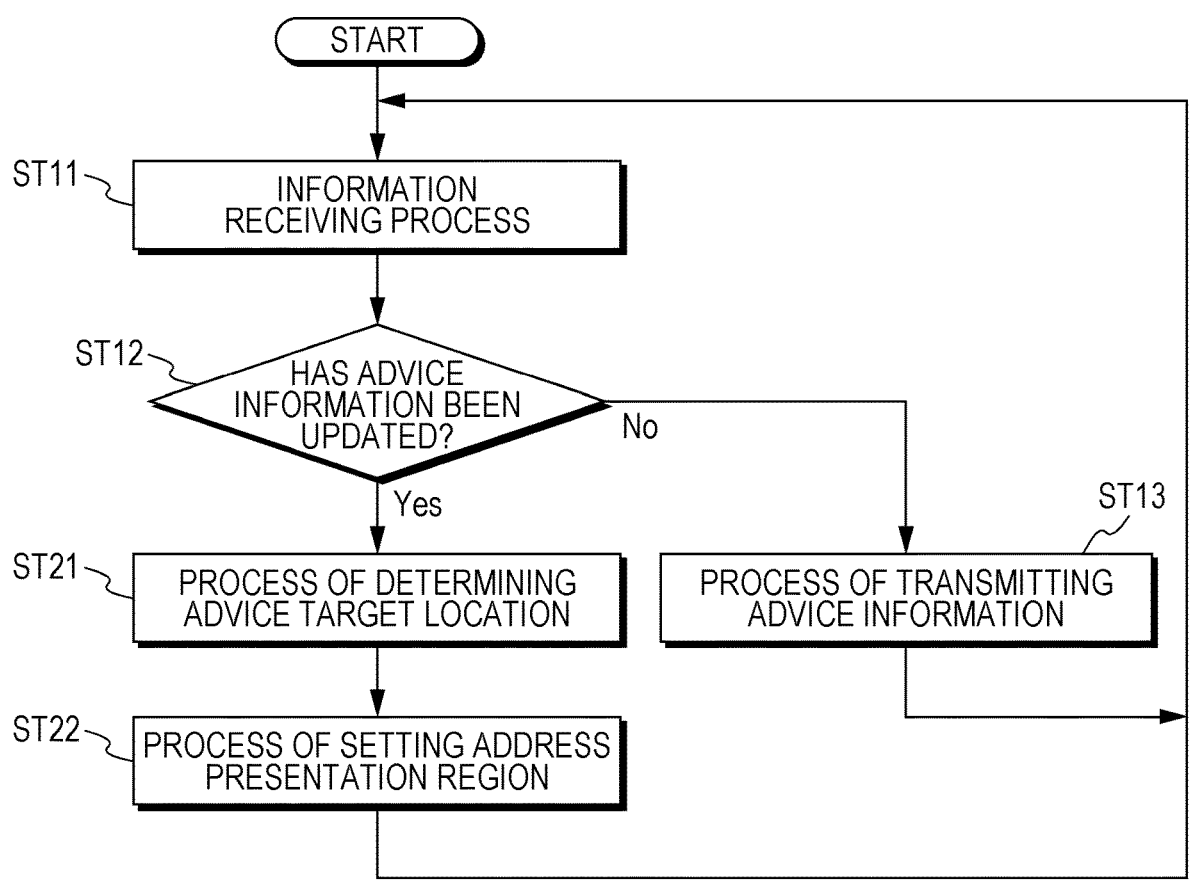
FIG. 6 is a flowchart showing operation of the server device.

FIG. 6 is a flowchart showing operation of the server device 50. In step ST11, the server device 50 performs an information receiving process. The server device 50 receives information transmitted from each terminal device 20, accumulates the information in the storage unit 52, for example, and then moves on to step ST12.

In step ST12, the server device 50 determines whether advice information is to be updated. The server device 50 moves on to step ST21 if the advice information is to be updated, and moves on to step ST13 if the advice information is not to be updated. The advice information may be updated at predetermined time intervals or every time a predetermined period of time has passed, or may be updated every time the amount of information supplied from each terminal device 20 reaches a predetermined amount.

In step ST13, the server device 50 performs an advice information transmitting process. In a case where location information for presenting advice information is sent from each terminal device 20, the server device 50 generates advice information containing information indicating the advice presentation region located in a predetermined range based on the location indicated by the sent location information. The server device 50 further transmits the generated advice information to the terminal device 20 that has requested the advice information, and then returns to step ST11.

In step ST21, the server device 50 performs an advice target location determining process, and then moves to step ST22. In step ST22, the server device 50 performs an advice presentation region setting process.

Figure 7:
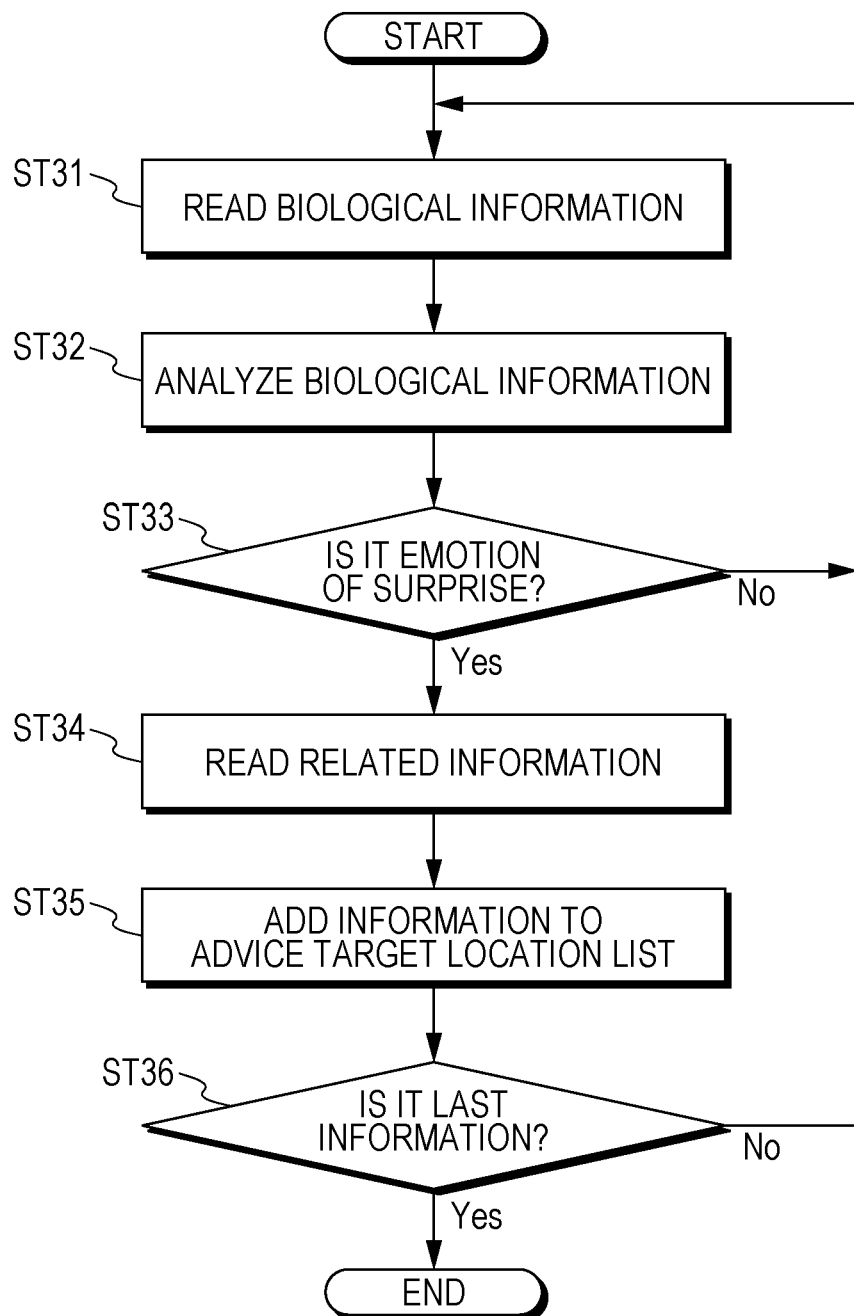
FIG. 7 is a flowchart showing an advice target location determining process.

FIG. 7 is a flowchart showing the advice target location determining process. In step ST31, the server device 50 reads biological information. The server device 50 reads the biological information accumulated in the storage unit 52, and then moves on to step ST32.

In step ST32, the server device 50 analyzes the biological information. The server device 50 analyzes the biological information, estimates in what state of emotion the driver or the pedestrian using the terminal device 20 is, and then moves on to step ST33.

In step ST33, the server device 50 determines whether the emotion is surprise. The server device 50 moves on to step ST34 if the driver or the pedestrian using the terminal device 20 has an emotion of surprise, and returns to step ST31 when the driver or the pedestrian has some other emotion.

In step ST34, the server device 50 reads related information. The server device 50 reads the location information and the transportation means information associated with the biological information determined to be an emotion of surprise from the storage unit 52, and then moves on to step ST35.

In step ST35, the server device 50 adds the information to the advice target location list. The server device 50 adds the location at which the driver or the pedestrian using the terminal device 20 had the emotion of surprise, as the advice target location to the list, and then moves on to step ST36.

In step ST36, the server device 50 determines whether the information is the last piece of information. The server device 50 returns to step ST31 if unread biological information remains in the storage unit 52, and ends the advice target location determining process if the read biological information is the last piece of biological information.

FIGS. 8A-8C show an example operation in the advice target location determining process. FIG. 8A shows an example of the biological information stored in the storage unit 52, such as the numbers of heart beats, In a case where the number of heart beats (the number of heart beats in 10 seconds, for example) is larger a predetermined threshold value (10, for example), the server device 50 determines the emotion to be surprise. Therefore, it is determined that the user had an emotion of surprise during the period "2012/05/18 9:31:00~09".

FIG. 8B shows an example of the location information and the transportation means information associated with the biological information. The location information and the transportation means information are associated with the biological information based on the time information. Therefore, the location information (latitude and longitude) "xx.6894934, yyy. 6917221" and the transportation means information "vehicle" during the period "2012/05/18 9:31: 00~09" are added to the advice target location list shown in FIG. 8C.

Figure 9:
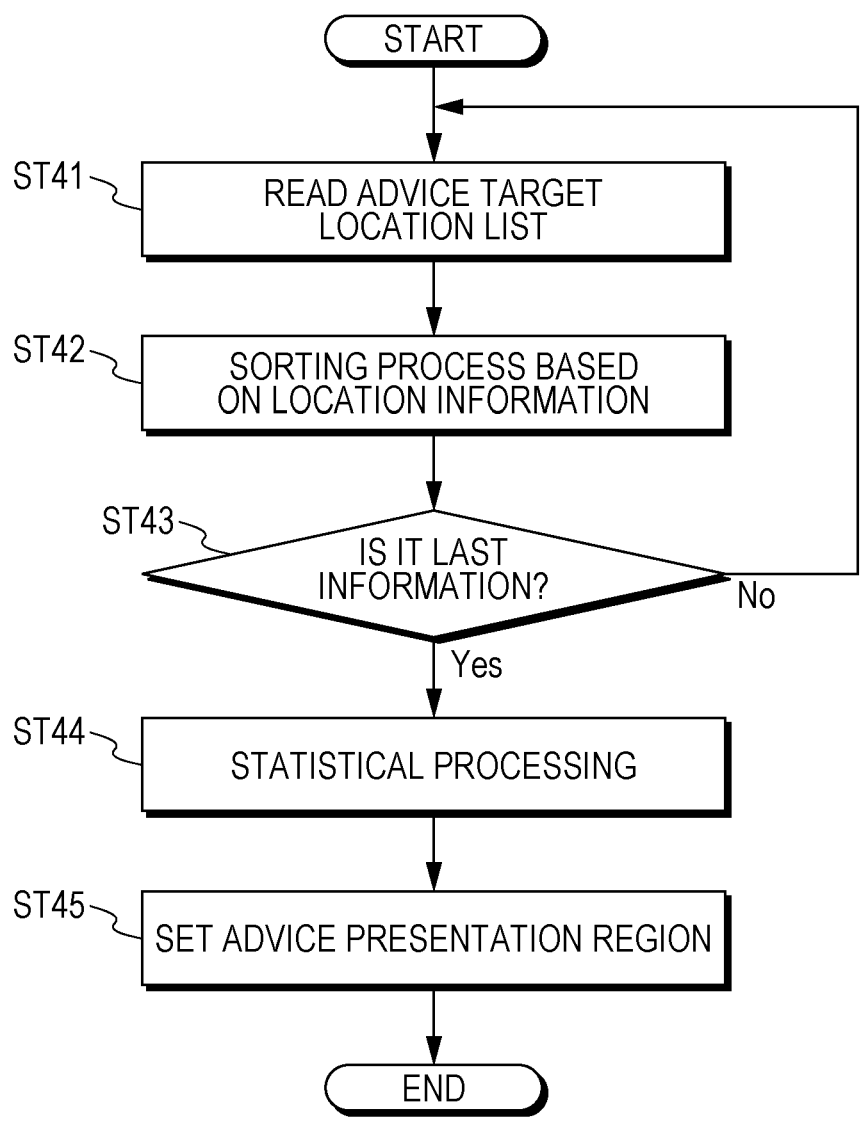
FIG. 9 is a flowchart showing an advice presentation region setting process.

FIG. 9 is a flowchart showing an advice presentation region setting process. In step ST41, the server device 50 reads the advice target location list. The server device 50 reads the advice target location list stored in the storage unit 52, and then moves on to step ST42.

In step ST42, the server device 50 performs a sorting process based on the location information for each transportation means. The server device 50 sorts out an advice target location based on the location information, for each transportation means information indicated by the transportation means information. The server device 50 divides the region based on latitude and longitude, for example, sets the respective divisional regions as advice presentation candidate regions, allocates the advice target location to the corresponding advice presentation candidate region for each transportation means, and then moves on to step ST43.

In step ST43, the server device 50 determines whether the information is the last piece of information. The server device 50 returns to step ST41 if unread information in the advice target location list remains in the storage unit 52, and moves on to step ST44 if the read information is the last piece of information in the advice target location list.

In step ST44, the server device 50 performs statistical processing for each transportation means. The server device 50 calculates, for each transportation means, a statistical value or the average number of advice target locations allocated to each advice presentation candidate region, and then moves on to step ST45.

In step ST45, the server device 50 sets an advice presentation region for each transportation means. The server device 50 sets a threshold value in accordance with the statistical value calculated through the statistical processing in step ST44. Further, the server device 50 compares the number of advice target locations allocated to each advice presentation candidate region with the set threshold value for each transportation means. Based on the comparison result, the server device 50 sets the advice presentation region(s) that is the advice presentation candidate region(s) with a larger number of advice target locations than the threshold value, and then ends the advice presentation region setting process.

FIG. 10 is a diagram for explaining an operation in the advice presentation region setting process. FIG. 10 shows an example of an advice target location list generated for each terminal device. FIG. 10 shows an advice target location list in which the transportation means is "vehicle" based on the transportation means information.

The server device 50 divides the region based on latitude and longitude, and calculates the number of advice target locations included in a region at latitude "xx.6894000 to xx.6895000" and longitude "yyy.6917000 to yyy.6918000" (equivalent to one advice presentation candidate region), for example. In the example shown in FIG. 10, six lists surrounded by dashed lines are included in the region, and therefore, the number of advice target locations is "6". The threshold value is set based on the statistical value obtained by performing statistical processing with the use of the numbers of advice target locations in the respective advice presentation candidate regions, and the advice presentation region(s) with a larger number of advice target locations than the threshold value is set as the advice presentation region(s). In a case where the average number of advice target locations in each advice presentation candidate region is "2", and the threshold value is set as the value twice the average value, for example, the region at latitude "xx.6894000 to xx.6895000" and longitude "yyy.6917000 to yyy.6918000" is set as the advice presentation region, since the number of advice target locations included in this region is "6".

Although an example process in a case where the transportation means is "vehicle" is shown in FIG. 10, the server device 50 performs such a process for each transportation means, sets an advice presentation region for each transportation means, and stores advice information containing the information indicating the advice presentation region into the storage unit 52.

Figure 11:
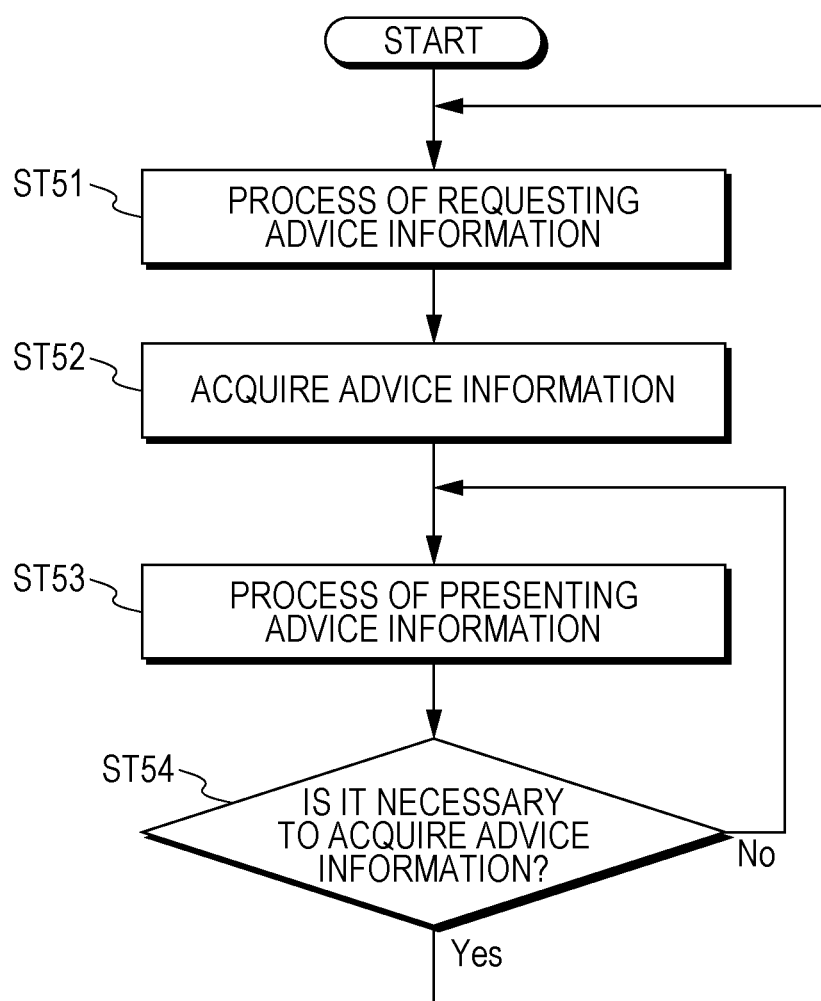
FIG. 11 is a flowchart showing an advice presenting operation of a terminal device.

Next, a case where a terminal device performs an advice presenting operation is described. FIG. 11 is a flowchart showing an advice presenting operation of a terminal device.

In step ST51, a terminal device 20 performs an advice information requesting process. The terminal device 20 transmits an advice information request containing the information indicating the current location of the terminal device 20, to the server device 50. In a case where advice information about a predetermined range based on a desired location has not been acquired, for example, an advice information request is transmitted.

In step ST52, the terminal device 20 acquires advice information. The terminal device 20 further receives advice information supplied from the server device 50 in response to the advice information request, and then moves on to step ST53.

In step ST53, the terminal device 20 performs an advice information presenting process. The terminal device 20 presents the acquired advice information through the display unit 41 or the audio output unit 43, and then moves on to step ST54.

In step ST54, the terminal device 20 determines whether advice information needs to be acquired. The terminal device 20 returns to step ST53 if the advice information about a predetermined region based on the current location has been acquired, and returns to step ST51 if advice information has not been acquired and needs to be acquired.

In accordance with the advice information acquired from the server device 50, the terminal device 20 determines an advice presentation region located in the predetermined range based on the current location. Further, the terminal device 20 performs advice presentation as to the determined advice presentation region. For example, the terminal device 20 determines an advice presentation region located in a map range displayed on the display unit 41, and displays an icon or the like that indicates the contents of advice in a distinguishable manner at the location of the advice presentation region on the map.

If there are many advice presentation regions in a map range, the map becomes hard to see when icons or the like are displayed at the locations of the advice presentation regions. The terminal device 20 determines the advice presentation region through which a vehicle or a pedestrian is about to pass based on the traveling direction of the vehicle or the pedestrian, path information in navigation, the log of location information, and the like. Further, the terminal device 20 may present advice in the form of an image or voice in a case where a vehicle or a pedestrian approaches an advice presentation region.

In a case where the terminal device 20 is provided in a vehicle, icons indicating advice presentation regions are displayed on the map. When the vehicle is at a certain short distance (10 m, for example) from an advice presentation region, voice is emitted to the effect that an advice presentation region is 10 m ahead. In a case where a navigation function is used, a route to avoid advice presentation regions is searched for, and after the search, the driver may be notified that advice presentation regions are avoided.

In a case where a pedestrian owns the terminal device 20, and uses a navigation function and a music reproduction function, voice is emitted to the effect that an advice presentation region is 10 m ahead when the pedestrian is at a certain distance (10 m, for example) from an advice presentation region.

In a case where the terminal device 20 has a vibration function, advice is presented by notifying that an advice presentation region is at a certain distance through vibration. In a case where the terminal device 20 has a mail transmission/reception function, when the user approaches a dangerous point, a notification of the dangerous point may be issued by transmitting e-mail to the owned portable device.

As information about the transportation means is included in the advice information, advice as to its own transportation means and a different transportation means from its own transportation means is presented. For example, advice as to a location at which a pedestrian had an emotion of surprise is given to the driver of a vehicle through an image or voice. In this manner, the driver can recognize the location the pedestrian found dangerous, and the driver can be prevented from being distracted at the location where pedestrians become careful. Likewise, advice as to a location at which the driver of a vehicle had an emotion of surprise is given to a pedestrian, so that the pedestrian can recognize the location the driver found dangerous, and the pedestrian can be prevented from being distracted at the location where drivers become careful. Thus, accidents and the like can be prevented. Also, advice related to a vehicle as a transportation means is given to the driver of a vehicle, so that the driver can recognize beforehand the locations other drivers found dangerous.

<5. Other Structures and Operations>

Figure 12:
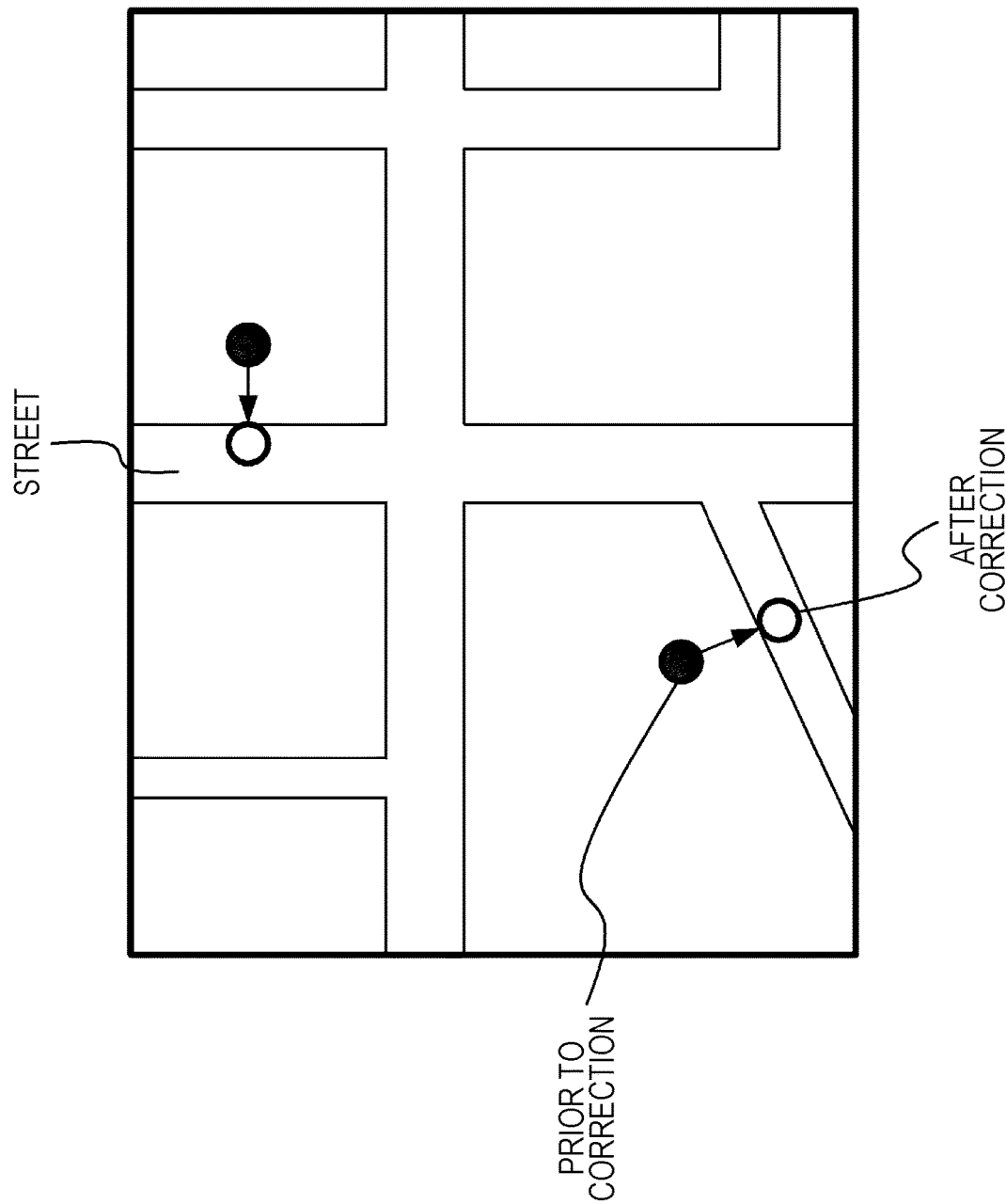
FIG. 12 shows an example of a location information correcting operation.

In some cases, location information to be supplied from a terminal device 20 to the server device 50 includes an error with respect to an actual location due to a location measurement error or the like. Here, a location at which a driver or a pedestrian had an emotion of surprise is on a street, and therefore, the server device 50 performs correction so that the location information indicates the location on the street. In a case where the location indicated by the acquired location information is not on a street as a result of a search for the nearest street in map data based on the acquired location information, the location information is corrected so that the location information indicates a location on the nearest street, for example. The server device 50 provides advice information based on the corrected location information. For example, in a case where locations (black circles) indicated by acquired location information are not on streets as shown in FIG. 12, the location information is corrected so that the location information indicates locations (white circles) on streets. If location information is corrected in this manner, advice presentation regions can be set with high precision. The location information correction is performed by the determining unit 601 of the control unit 60, for example. The location information correction may be performed when the location information is stored into the storage unit 52, or may be performed when an advice target location is determined based on the location information.

Figure 13:
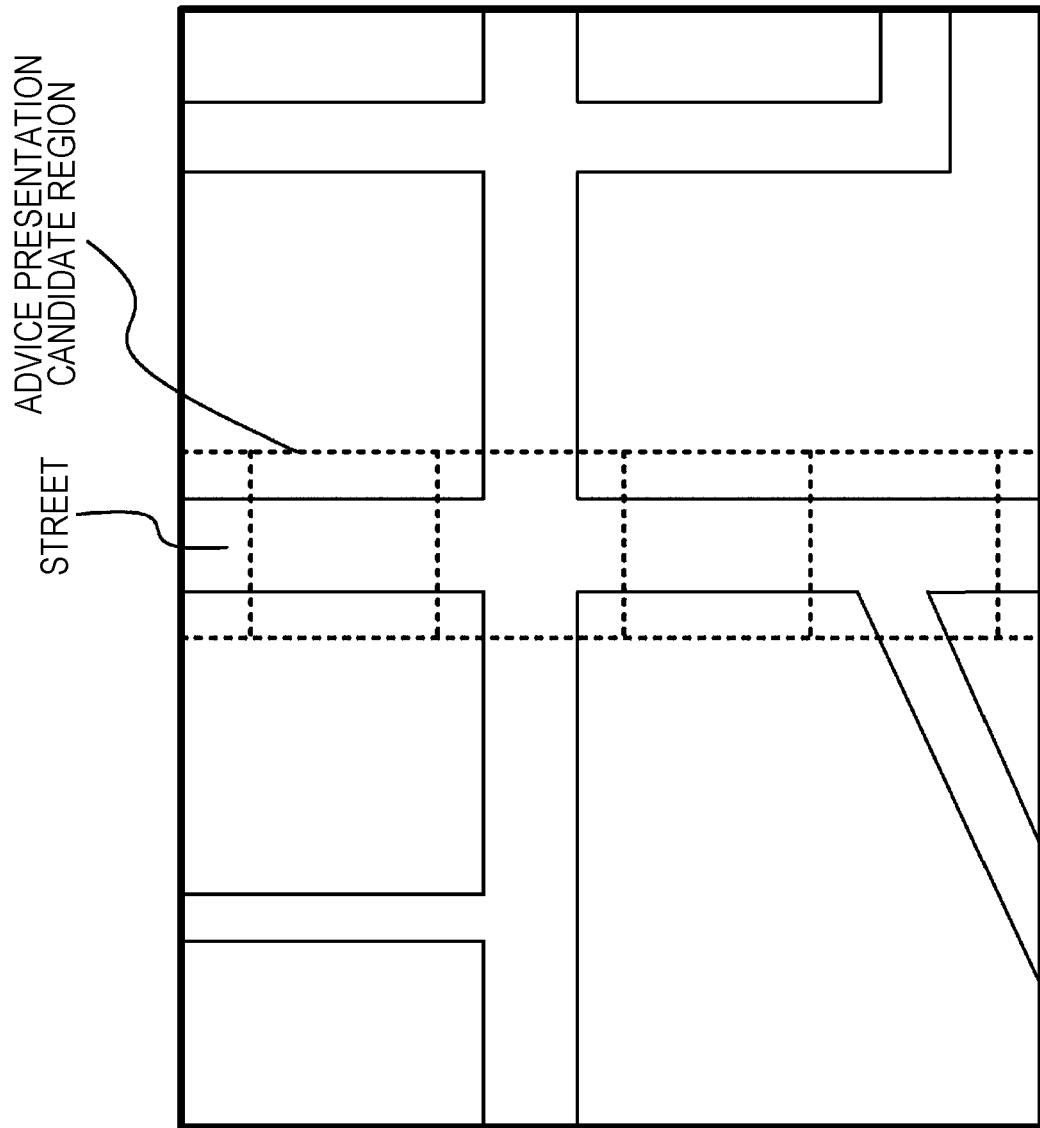
FIG. 13 shows an example of an advice presentation candidate region setting operation.

Since the locations at which a driver or a pedestrian had an emotion of surprise are locations on streets, advice presentation candidate regions are set along a street, so that advice presentation regions can be efficiently set. For example, the server device 50 acquires information (a latitude/longitude stream) about a street from map data, and sets advice presentation candidate regions (regions indicated by dashed lines) along the street by dividing the street at certain intervals as shown in FIG. 13. As advice presentation candidate regions are set in this manner, no advice presentation candidate regions are set outside the streets, and advice presentation regions can be efficiently set. Although the advice presentation candidate regions are square regions in FIG. 13, ranges of a predetermined distance as a radius of several meters from locations at certain intervals, for example, may be set as advice presentation candidate regions.

Furthermore, the sizes of the advice presentation candidate regions may be varied depending on the map data. For example, at an intersection, an advice presentation candidate region is set so as to include the intersection. At a location that does not include any intersection, building, or the like, the advice presentation candidate region is made larger in size. In this manner, advice presentation candidate regions can be efficiently set in accordance with a traffic condition or the like.

In the above described embodiment, advice information indicating advice presentation regions is supplied from the server device 50 to the terminal devices 20. However, the advice information may contain presentation information as to what kind of advice is to be presented. In a case where a terminal device 20 can selectively present more than one piece of advice, select information for selecting the piece of advice to be presented may be included in the advice information. In this manner, the pieces of advice to be presented by the terminal devices 20 can be managed by the server device 50. For example, threshold values may be set based on a statistical value, advice presentation regions may be classified, advice such as a "caution" may be issued in an advice presentation region including a large number of advice target locations, and advice such as an "alert" may be issued in an advice presentation region including an extremely large number of advice target locations. If the advice information includes time information, advice can be presented only during the hours at which many locations where users had an emotion of surprise were detected.

In the above described embodiment, biological information is transmitted from the terminal devices 20 to the server device 50, and the server device 50 estimates emotions. However, the terminal devices 20 may estimate emotions, and transmit information about the locations where users had an emotion of surprise or location information about the advice target locations, the results of the emotion estimation, and transportation means determination information, or location information about the advice target locations and transportation means determination information, to the server device 50. For example, the emotion estimating unit 39 may be provided as indicated by a dashed line in FIG. 2, estimate an emotion based on biological information acquired by the biological information acquiring unit 34, determine an advice target location that is the location indicated by the location information associated with the biological information when a predetermined emotion is estimated, and supply the location information and transportation means determination information to the server device 50. In this case, the server device 50 performs statistical processing on the location information about the advice target locations for each transportation means based on the transportation means determination information supplied from each terminal device 20, and determines advice presentation regions. As a result, the processing to be performed by the server device 50 can be reduced. Alternatively, the functions of the server device 50 may be provided in the terminal devices 20, and a terminal device 20 may acquire location information, biological information, and transportation means information from another terminal device 20, set advice presentation regions, and present advice as to the advice presentation regions.

Furthermore, in a case where advice as to a location a driver or a pedestrian found dangerous is to be presented, an advice presentation region may be determined by taking geographical conditions into account. For example, in a case where a location a user found dangerous is an intersection, a narrow street, or in the vicinity of a school, the threshold value to be compared with the number of advice target locations is made smaller, the number of advice target locations is weighted, or a value in accordance with geographical conditions is added to the number of advice target locations, so that an advice presentation region can be readily determined. In this manner, the frequency at which a dangerous point is determined can be increased at such locations.

Although an advice presentation region is set by determining advice target locations to be locations where drivers or pedestrians had an emotion of surprise, an advice presentation region may be set by determining advice target locations to be the locations where drivers felt sleepy. Alternatively, desired locations are determined based on results of estimation of some other emotion, and advice may be issued based on results of the determination.

The series of processes described in this specification can be performed by hardware, software, or a combination of hardware and software. In a case where processes are performed by software, a program in which the process sequences are recorded is installed in a memory incorporated into special-purpose hardware in a computer. Alternatively, the processes can also be performed by installing the program into a general-purpose computer that can perform various kinds of processes.

For example, the program can be recorded beforehand on a hard disk or a ROM (Read Only Memory) as a recording medium. Alternatively, the program can be temporarily or permanently stored (recorded) in a removable recording medium such as a flexible disk, a CD-ROM (Compact Disc Read Only Memory), an MO (Magneto-Optical) disk, a DVD (Digital Versatile Disc), a magnetic disk, or a semiconductor memory card. Such a removable recording medium can be provided as so-called packaged software.

The program may not only be installed from a removable recording medium into a computer, but also be transferred in a wireless or wired manner from a download site to a computer via a network such as a LAN (Local Area Network) or the Internet. The computer receives the program transferred in such a manner, and can install the program into a recording medium such as an internal hard disk.

It should be noted that the present technique should not be interpreted being limited to the above described embodiment of the technique. The embodiment of this technique discloses the present technique through examples, and it should be obvious that those skilled in the art can modify or replace those embodiments with other embodiments without departing from the scope of the technique. That is, the claims should be taken into account in understanding the subject matter of the technique.

An information processing apparatus of the present technique may also have structures described below.

(1) An information processing apparatus including:
a determining unit that determines an advice target location at which advice needs to be presented for each transportation means based on location information, biological information, and transportation means information; and
a presentation region setting unit that sets an advice presentation region where advice is to be presented based on the advice target location determined by the determining unit.

(2) The information processing apparatus according to (1), wherein the determining unit estimates an emotion based on the biological information, and determines the advice target location to be the location of acquirement of the biological information when a predetermined emotion is estimated.

(3) The information processing apparatus according to (2), wherein the determining unit determines the advice target location by taking into account geographical conditions.

(4) The information processing apparatus according to any of (1) through (3), wherein the determining unit performs correction so that the location information indicates a location on a street.

(5) The information processing apparatus according to any of (1) through (4), wherein the presentation region setting unit performs statistical processing on a result of the determination on the advice target location in an advice presentation candidate region, and sets the advice presentation candidate region as an advice presentation region based on a result of the processing.

(6) The information processing apparatus according to any of (1) through (5), wherein the presentation region setting unit sets the advice presentation candidate region by dividing a region of a street.

(7) The information processing apparatus according to any of (1) through (6), further including
a communication unit,
wherein the determining unit determines the advice target location based on location information, biological information, and transportation means information, the location information, the biological information, and the transportation means information being received by the communication unit.

(8) The information processing apparatus according to (7), further including
an advice information transmission processing unit,
wherein the advice information transmission processing unit selects an advice presentation region based on the location information indicated by an advice information request received by the communication unit, and transmits advice information indicating the selected advice presentation region to the requester that has requested the advice information.

(9) The information processing apparatus according to (8), wherein the advice information transmission processing unit transmits the advice information indicating on which transportation means the advice presentation region is based.

(10) The information processing apparatus according to (8), wherein the advice information transmission processing unit transmits the advice information including presentation information indicating what kind of advice is to be presented.

(11) The information processing apparatus according to any of (1) through (10), further including
an advice presenting unit that presents advice as to the advice presentation region.

(12) An information processing apparatus including:
a location information acquiring unit that acquires location information;

a biological information acquiring unit that acquires biological information about a user;
a transportation means identifying unit that identifies the transportation means of the user;
a communication unit;
a control unit that transmits the location information acquired by the location information acquiring unit, the biological information acquired by the biological information acquiring unit, and transportation means information indicating the transportation means identified by the transportation means identifying unit from the communication unit to an information processing apparatus that provides advice information, the location information, the biological information, and the transportation means information being associated with one another; and
an advice presenting unit that presents advice based on the advice information received by the communication unit.

(13) The information processing apparatus according to (12), wherein the control unit transmits a request for the advice information to the information processing apparatus that provides the advice information, the request containing location information indicating a desired location.

(14) The information processing apparatus according to (13), wherein, when advice information about a predetermined range based on the desired location has not been acquired, the control unit transmits the request for the advice information.

(15) The information processing apparatus according to any of (12) through (14), wherein the advice presenting unit determines an advice presentation region through which the information processing apparatus is about to pass based on information about the advice presentation region, the information being contained in the advice information, and presents advice as to the determined advice presentation region.

(16) The information processing apparatus according to any of (12) through (15), wherein, when the advice information contains presentation information indicating what kind of advice is to be presented, the advice presenting unit presents advice based on the presentation information.

(17) The information processing apparatus according to any of (12) through (15), further including
an emotion estimating unit that estimates an emotion being felt by the user based on the biological information acquired by the biological information acquiring unit,
wherein the control unit transmits location information indicating the location of the acquerement of the biological information when the emotion estimating unit estimates a predetermined emotion, the location information indicating the location of the acquerement of the biological information being associated with the transportation means information.

INDUSTRIAL APPLICABILITY

In an information processing apparatus, an information processing method, and an information processing system of this technique, an advice target location at which a user had a predetermined emotion, for example, is determined for each transportation means based on location information, biological information, and transportation means information, and an advice presentation region is set based on the advice target location. Also, advice as to the set advice presentation region is presented. Accordingly, effective advice for preventing accidents can be presented to users such as drivers or pedestrians. For example, locations pedestrians find dangerous can be presented to drivers, and locations drivers find dangerous can be presented to pedestrians. Accordingly, accidents and the like can be prevented. Therefore, this technique is suitable for electronic devices such as a navigation apparatus and a portable communication terminal that have a function to generate location information indicating current location, and biological information.

REFERENCE SIGNS LIST

10 Information processing system
20 Terminal device
21 Z-axis gyro sensor
22 Y-axis gyro sensor
23 Triaxial acceleration sensor
24 Geomagnetic sensor
25 Atmospheric pressure sensors
28, 29 Antenna
31 Navigation unit
33 Transportation means identifying unit
34 Biological information acquiring unit
35 Communication unit
39 Emotion estimating unit
41 Display unit
42 Storage unit
43 Audio output unit
44 User interface unit
45 Control unit
50 Server device
51 Communication unit
52 Storage unit
53 Input unit
54 Output unit
60 Control unit
90 Network
311 Angle calculating unit
312 Velocity calculating unit
313 Location calculating unit
314 Attitude angle detecting unit
315 Orientation calculating unit
316 Positioning signal processing unit
317 Altitude calculating unit
319 Navigation processing unit
601 Determining unit
602 Presentation region setting unit
603 Advice information transmission processing unit

The invention claimed is:

1. An information processing apparatus comprising: hardware circuitry configured to
receive location information of a vehicle from a first terminal device and biological information of a driver of the vehicle from a second terminal device, wherein the first terminal device is attached to the vehicle and the second terminal device is attached to the driver of the vehicle and includes at least one sensor that acquires the biological information,
determine an advice target location at which advice is to be presented, wherein the advice target location is determined based on log information including the location information received from the first terminal device and the biological information received from the second terminal device,
set a navigation route based on the determined advice target location and current location information, wherein the navigation route does not include the determined advice target location, provide the navigation route to the driver, and display an icon indicating the determined advice target location and contents of the advice on a display attached to the vehicle.

2. The information processing apparatus according to claim 1, wherein, the hardware circuitry is further configured to estimate an emotion based on the biological information, and determine the advice target location to be a location of acquirement of the biological information received from the second terminal device when a predetermined emotion is estimated.

3. The information processing apparatus according to claim 2, wherein the hardware circuitry is configured to determine the advice target location based on a geographical condition.

4. The information processing apparatus according to claim 1, wherein, the hardware circuitry is configured to perform statistical processing on a result of the determination on the advice target location in an advice presentation candidate region, and set the advice presentation candidate region as an advice presentation region where the advice is to be presented based on a result of the statistical processing.

5. The information processing apparatus according to claim 1, wherein the hardware circuitry is configured to set an advice presentation region where the advice is to be presented in accordance with a location on a street.

6. The information processing apparatus according to claim 5, wherein the hardware circuitry is configured to provide the advice to the driver in order to follow the navigation route to avoid the location on the street corresponding to the set advice presentation region.

7. An information processing method comprising:

receiving location information of a vehicle from a first terminal device and biological information of a driver of the vehicle from a second terminal device, wherein the first terminal device is attached to the vehicle and the second terminal device is attached to the driver of the vehicle and includes at least one sensor that acquires the biological information;

determining an advice target location at which advice is to be presented, wherein the advice target location is determined based on log information including the location information received from the first terminal device and the biological information received from the second terminal device;

setting a navigation route based on the determined advice target location and current location information, wherein the navigation route does not include the determined advice target location;

providing the navigation route to the driver; and displaying an icon indicating the determined advice target location and contents of the advice on a display attached to the vehicle.

8. A non-transitory computer-readable medium having embodied thereon a program, which when executed by a computer, causes the computer to execute a method, the method comprising:

receiving location information of a vehicle from a first terminal device and biological information of a driver of the vehicle from a second terminal device, wherein the first terminal device is attached to the vehicle and the second terminal device is attached to the driver of the vehicle and includes at least one sensor that acquires the biological information;

determining an advice target location at which advice is to be presented, wherein the advice target location is determined based on log information including the location information received from the first terminal device and the biological information received from the second terminal device;

setting a navigation route based on the determined advice target location and current location information, wherein the navigation route does not include the determined advice target location;

providing the navigation route to the driver; and displaying an icon indicating the determined advice target location and contents of the advice on a display attached to the vehicle.

9. The information processing apparatus according to claim 1, wherein the hardware circuitry is further configured to present the advice using a voice when the vehicle is within a threshold distance of the advice target location.

* * * * *